(12) United States Patent
Hardin

(10) Patent No.: US 8,043,316 B2
(45) Date of Patent: Oct. 25, 2011

(54) ADJUSTABLE SPACER

(75) Inventor: Terry D. Hardin, Irvine, CA (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 824 days.

(21) Appl. No.: 12/114,294

(22) Filed: May 2, 2008

(65) Prior Publication Data
US 2009/0275858 A1 Nov. 5, 2009

(51) Int. Cl.
*A61B 17/32* (2006.01)
*A61B 10/00* (2006.01)

(52) U.S. Cl. ........ 606/172; 606/167; 606/170; 600/562; 600/567

(58) Field of Classification Search ........... 606/167, 606/170, 172; 600/562, 567
See application file for complete search history.

(56) References Cited

U.S. PATENT DOCUMENTS

| | | | |
|---|---|---|---|
| 3,682,177 A * | 8/1972 | Ames et al. | 606/172 |
| 4,177,814 A | 12/1979 | Knepshield et al. | |
| 4,766,907 A * | 8/1988 | de Groot et al. | 600/567 |
| 4,781,198 A | 11/1988 | Kanabrocki | |
| 5,066,288 A * | 11/1991 | Deniega et al. | 604/274 |
| 5,133,359 A * | 7/1992 | Kedem | 600/567 |
| 5,183,465 A * | 2/1993 | Xanthakos et al. | 604/108 |
| 5,281,197 A | 1/1994 | Arias et al. | |
| 5,289,831 A | 3/1994 | Bosley | |
| 5,388,589 A * | 2/1995 | Davis | 600/567 |
| 5,439,005 A * | 8/1995 | Vaughn | 600/568 |
| 5,478,348 A * | 12/1995 | Bajada | 606/185 |
| 5,480,389 A * | 1/1996 | McWha et al. | 604/165.02 |
| 5,484,418 A * | 1/1996 | Quiachon et al. | 604/167.03 |
| 5,489,274 A * | 2/1996 | Chu et al. | 604/167.05 |
| 5,505,710 A * | 4/1996 | Dorsey, III | 604/158 |
| 5,647,374 A | 7/1997 | Cutrer | |
| 5,743,916 A * | 4/1998 | Greenberg et al. | 606/102 |
| 5,782,764 A | 7/1998 | Werne | |
| 5,788,664 A * | 8/1998 | Scalise | 604/15 |
| 5,843,017 A * | 12/1998 | Yoon | 604/22 |
| 5,879,357 A * | 3/1999 | Heaton et al. | 606/116 |
| 5,890,897 A * | 4/1999 | Kruger et al. | 433/75 |
| 5,928,164 A * | 7/1999 | Burbank et al. | 600/567 |
| 5,938,604 A | 8/1999 | Wagner et al. | |
| 5,980,469 A * | 11/1999 | Burbank et al. | 600/567 |
| 6,083,177 A * | 7/2000 | Kobren et al. | 600/564 |

(Continued)

FOREIGN PATENT DOCUMENTS

DE 103 37 368 A1 3/2005

(Continued)

OTHER PUBLICATIONS

European Search Report #07251843.4-22318 dated Nov. 26, 2007.

(Continued)

*Primary Examiner* — Max Hindenburg
*Assistant Examiner* — Sean Dougherty
(74) *Attorney, Agent, or Firm* — Rader, Fishman & Grauer, PLLC

(57) ABSTRACT

A medical targeting and device introduction system includes an introducer having a cannula, and a hub. The cannula is defined, at least in part, by an inner lumen. The hub includes a latch to releasably secure the hub to a biopsy device. The hub includes a proximal end and a distal end. The latch extends from the proximal end, and the hemostatic valve is interposed within the introducer.

16 Claims, 9 Drawing Sheets

U.S. PATENT DOCUMENTS

| | | | |
|---|---|---|---|
| 6,161,034 A | 12/2000 | Burbank et al. | |
| 6,165,137 A * | 12/2000 | Milliman et al. | 600/567 |
| 6,213,988 B1 | 4/2001 | McIvor et al. | |
| 6,228,049 B1 * | 5/2001 | Schroeder et al. | 604/93.01 |
| 6,251,418 B1 | 6/2001 | Ahern et al. | |
| 6,272,372 B1 | 8/2001 | Fisher | |
| 6,276,661 B1 | 8/2001 | Laird | |
| 6,280,399 B1 | 8/2001 | Rossin et al. | |
| 6,336,914 B1 * | 1/2002 | Gillespie, III | 604/165.01 |
| 6,347,241 B2 | 2/2002 | Burbank et al. | |
| 6,494,844 B1 | 12/2002 | Van Bladel et al. | |
| 6,551,283 B1 * | 4/2003 | Guo et al. | 604/167.06 |
| 6,626,849 B2 | 9/2003 | Huitema et al. | |
| 6,628,982 B1 | 9/2003 | Thomas et al. | |
| 6,638,235 B2 | 10/2003 | Miller et al. | |
| 6,725,083 B1 | 4/2004 | Burbank et al. | |
| 6,744,824 B1 | 6/2004 | Duvaut et al. | |
| 6,863,676 B2 | 3/2005 | Lee et al. | |
| 7,044,957 B2 | 5/2006 | Foerster et al. | |
| 7,347,829 B2 * | 3/2008 | Mark et al. | 600/567 |
| 7,424,320 B2 * | 9/2008 | Chesbrough et al. | 600/431 |
| 7,708,751 B2 * | 5/2010 | Hughes et al. | 606/172 |
| 2001/0032649 A1 | 10/2001 | Nagano | |
| 2002/0016544 A1 | 2/2002 | Hareyama et al. | |
| 2002/0082519 A1 * | 6/2002 | Miller et al. | 600/566 |
| 2002/0120212 A1 | 8/2002 | Ritchart et al. | |
| 2003/0109801 A1 | 6/2003 | Rhad et al. | |
| 2003/0109803 A1 | 6/2003 | Huitema et al. | |
| 2003/0199753 A1 | 10/2003 | Hibner et al. | |
| 2003/0199754 A1 | 10/2003 | Hibner et al. | |
| 2003/0199785 A1 * | 10/2003 | Hibner et al. | 600/562 |
| 2003/0225343 A1 * | 12/2003 | Miller et al. | 600/567 |
| 2003/0233101 A1 | 12/2003 | Lubock et al. | |
| 2004/0006330 A1 * | 1/2004 | Fangrow, Jr. | 604/533 |
| 2004/0019297 A1 * | 1/2004 | Angel | 600/564 |
| 2004/0034280 A1 * | 2/2004 | Privitera et al. | 600/170 |
| 2004/0077938 A1 | 4/2004 | Mark et al. | |
| 2004/0077972 A1 | 4/2004 | Tsonton et al. | |
| 2005/0010134 A1 * | 1/2005 | Douglas et al. | 600/573 |
| 2005/0212175 A1 | 9/2005 | Tsonton et al. | |
| 2005/0215922 A1 | 9/2005 | Tsonton et al. | |
| 2005/0261581 A1 | 11/2005 | Hughes et al. | |
| 2005/0277829 A1 | 12/2005 | Tsonton et al. | |
| 2008/0097502 A1 * | 4/2008 | Winters-Hilt et al. | 606/172 |
| 2008/0161720 A1 * | 7/2008 | Nicoson et al. | 600/567 |
| 2008/0200834 A1 * | 8/2008 | Mark et al. | 600/566 |
| 2008/0228147 A1 * | 9/2008 | David-Hegerich et al. | 604/198 |
| 2009/0069697 A1 * | 3/2009 | Frazier et al. | 600/476 |
| 2009/0247900 A1 * | 10/2009 | Zimmer | 600/564 |
| 2009/0247901 A1 * | 10/2009 | Zimmer | 600/567 |
| 2009/0275858 A1 * | 11/2009 | Hardin | 600/567 |
| 2010/0004626 A1 * | 1/2010 | Miller et al. | 604/506 |
| 2010/0114031 A1 * | 5/2010 | Jarial et al. | 604/164.11 |

FOREIGN PATENT DOCUMENTS

| | | |
|---|---|---|
| EP | 1197180 A2 * | 4/2002 |
| JP | 06292677 A * | 10/1994 |
| WO | WO-98/22022 A1 | 5/1998 |
| WO | WO-9855016 | 12/1998 |
| WO | WO-01/54763 A2 | 8/2001 |
| WO | WO-2006037950 A | 4/2006 |

OTHER PUBLICATIONS

International Search Report #PCT/US03/26958 dated Apr. 2, 2004.

* cited by examiner

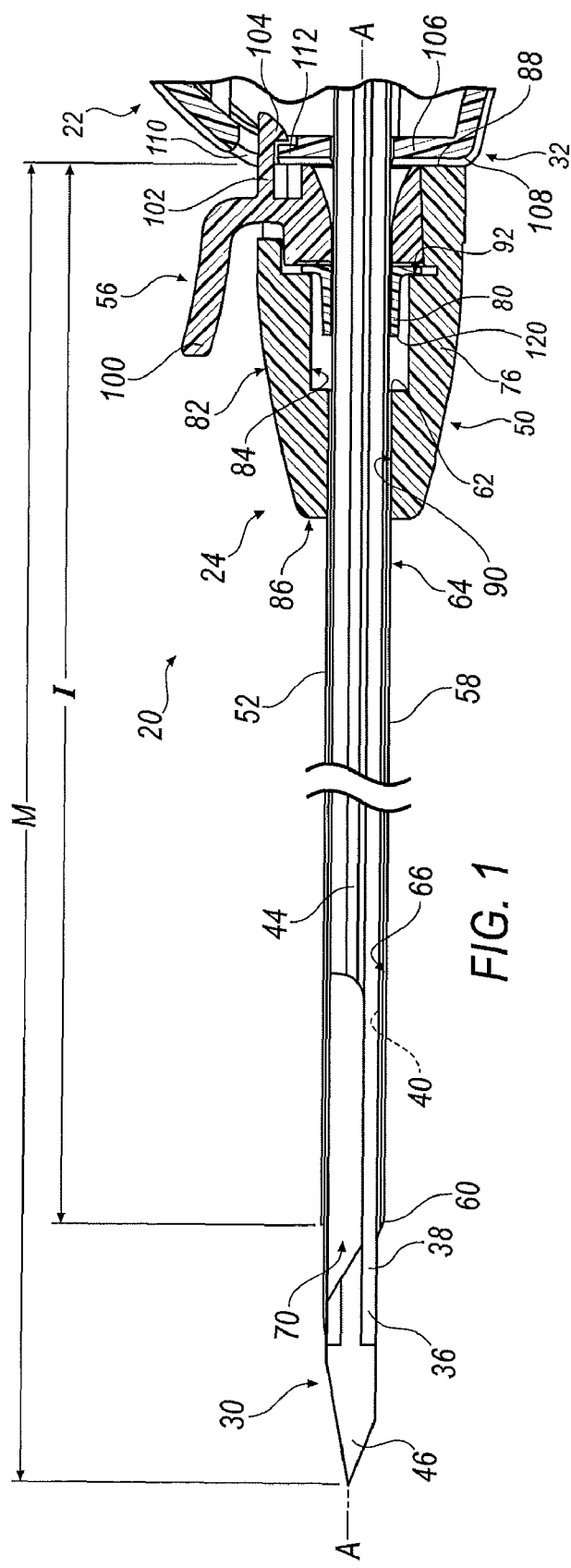

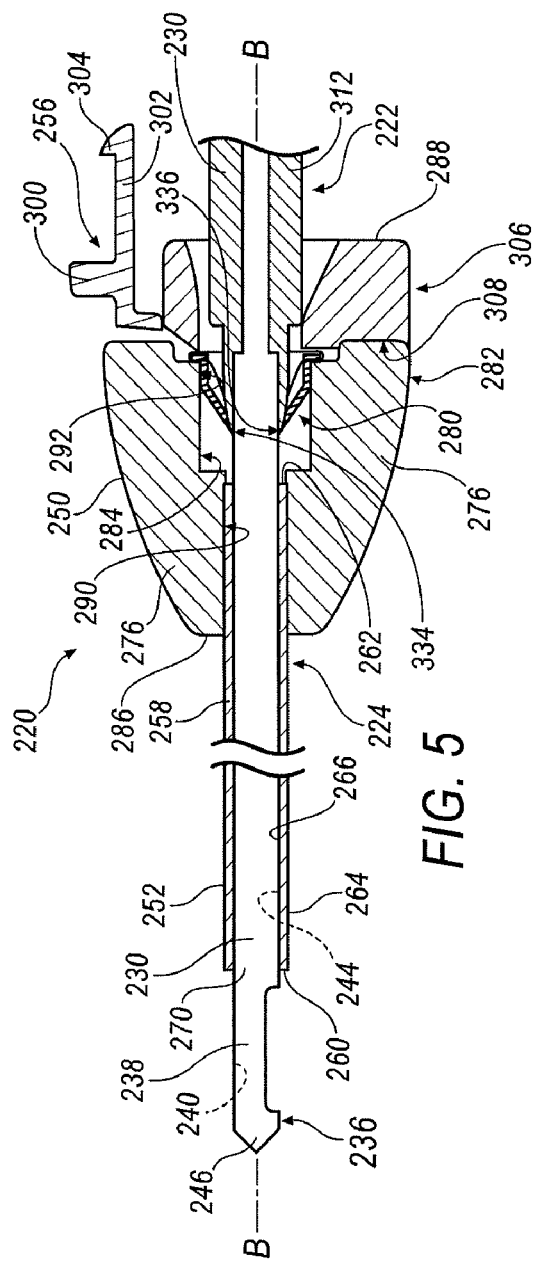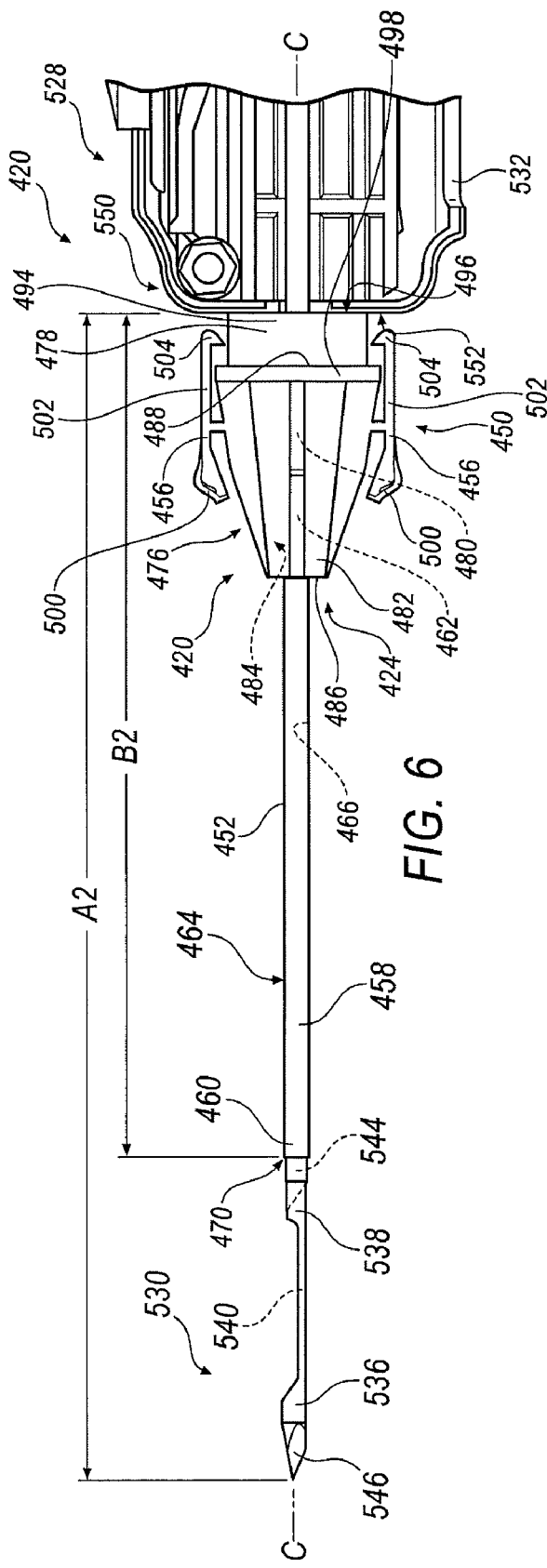

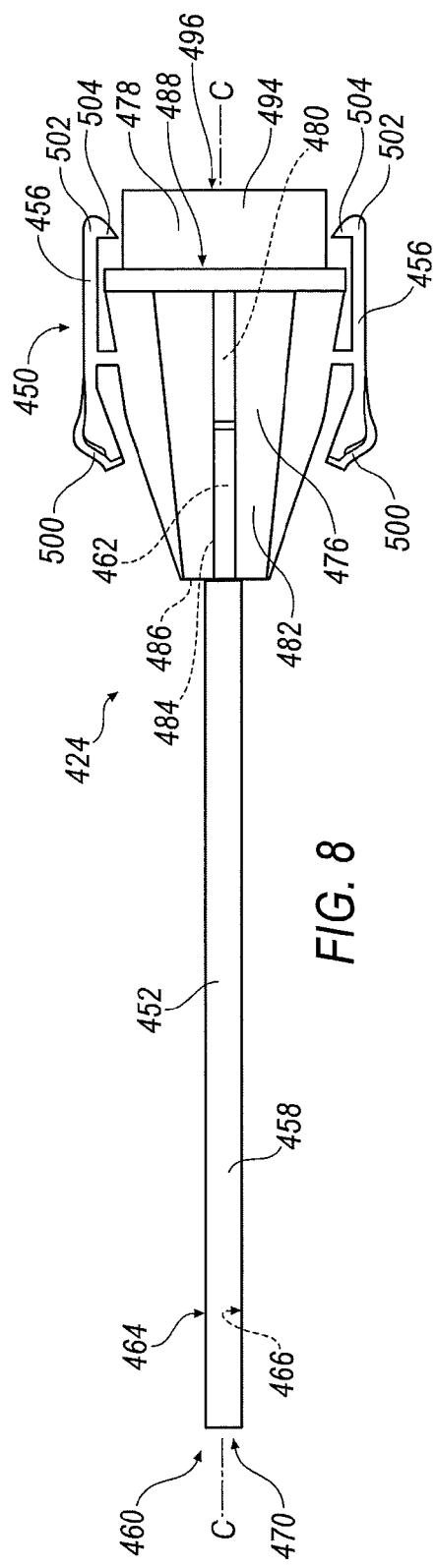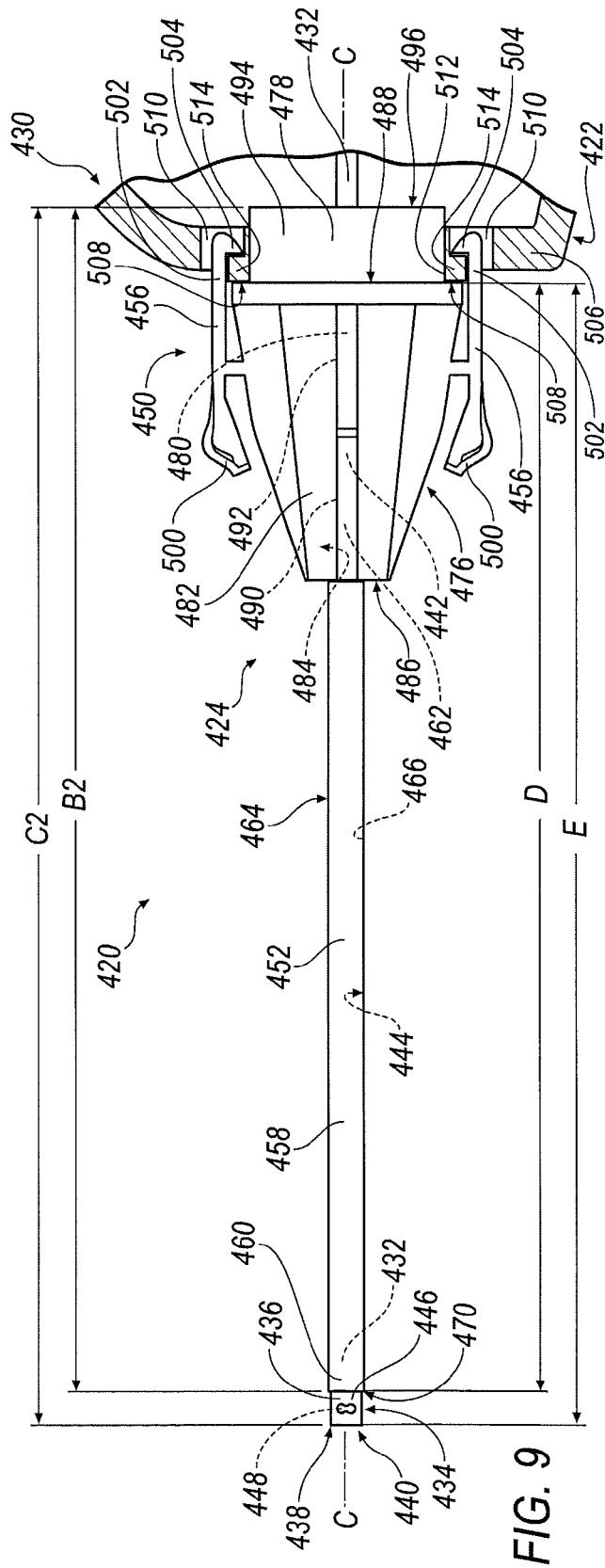

ADJUSTABLE SPACER

TECHNICAL FIELD

The present disclosure relates to the field of medical devices and more particularly to a medical system that permits introduction of, among other things, minimally invasive surgical instruments and other medical treatments into a patient's body.

BACKGROUND

Medical procedures have advanced to stages where less invasive or minimally invasive surgeries, diagnostic procedures and exploratory procedures have become desired and demanded by patients, physicians, and various medical industry administrators. To meet these demands, improved medical devices and instrumentation have been developed, such as cannula or micro-cannula, medical introducers, vacuum assisted biopsy apparatus, and other endoscopic related devices.

In the field of tissue biopsy, minimally invasive biopsy devices have been developed that require only a single insertion point into a patient's body to remove one or more tissue samples. One such biopsy device incorporates a "tube-within-a-tube" design that includes an outer piercing needle having a sharpened distal end and a lateral opening that defines a tissue receiving port. An inner cutting member is slidingly received within the outer piercing needle, which serves to excise tissue that has prolapsed into the tissue receiving port. A vacuum is used to draw the excised tissue into the tissue receiving port and aspirates the excised tissue from the biopsy site once severed.

Exemplary "tube-within-a-tube" biopsy devices are disclosed in U.S. Pat. Nos. 6,638,235 and 6,744,824, which are owned by the assignee of the present invention. Among other features, the exemplary biopsy devices can be used in conjunction with Magnetic Resonance Imaging (MRI). This compatibility is due to the fact that many of the components of the biopsy devices are made of materials that do not interfere with operation of MRI apparatus or are otherwise compatible therewith. It is desirable to perform biopsies in conjunction with MRI because it is a non-invasive visualization modality capable of defining the margins of a tumor.

Some biopsy devices may incorporate an introducer having an introducer cannula that may be placed over the biopsy needle extending from about the biopsy location to a location outside the patient. This introducer may remain in place after a biopsy is taken to permit the biopsy needle to be removed and a marker deployment device to be inserted within the introducer cannula in order to permit a marker to be positioned within the biopsy site. However, with differing sizes of outer cannula for biopsy needles and marker deployment devices, undesirable amounts of leakage between the outer cannula and the biopsy needle and/or marker deployment device may exist.

Additionally, biopsy needles and introducers are available in differing lengths, which demands that marker deployment devices be capable of sliding within the introducer a predetermined length for proper marker deployment. While a removable annular spacer positioned between the introducer hub and the marker deployment device may permit the marker deployment device to be inserted to a predetermined depth, interposing the marker deployment device within an annular spacer may increase the risk of contamination. Additionally, a spacer interposed between the introducer hub and the marker deployment device may not secure the introducer hub to the marker deployment device, thereby requiring a user to simultaneously deploy a marker while ensuring that the marker deployment device is properly positioned axially with respect to the desired marker deployment location.

While the exemplary MRI compatible biopsy devices have proven effective in operation, in some procedures it may be desirable to temporarily latch a biopsy device or marker deployment device to an introducer. A favorable introducer may also reduce leakage through the introducer cannula and provide for adjustability for the insertion depth of the marker deployment device.

SUMMARY

A medical targeting and device introduction system includes an introducer having a cannula, a hemostatic valve and a hub. The cannula is defined, at least in part, by an inner lumen. The hub includes a latch to releasably secure the hub to a biopsy device. The hub includes a proximal end and a distal end. The latch extends from the proximal end, and the hemostatic valve is interposed within the introducer.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are not intended to be exhaustive or otherwise limit or restrict the claims to the precise forms and configurations shown in the drawings and disclosed in the following detailed description.

FIG. 1 is a partially sectioned side view of a medical system according to an embodiment, with section graphics omitted for clarity.

FIG. 2 is a partially sectioned side view of a portion of the medical system of FIG. 1, with section graphics omitted for clarity.

FIG. 5 is a partially sectioned side view of the medical system of FIG. 4.

FIG. 6 is a partially sectioned side view of a medical system according to a further embodiment.

FIG. 8 is a side view of a portion of the medical system of FIG. 6.

FIG. 9 is a partially sectioned side view of a medical system of FIG. 6, illustrating additional components.

DETAILED DESCRIPTION

Figure 3:
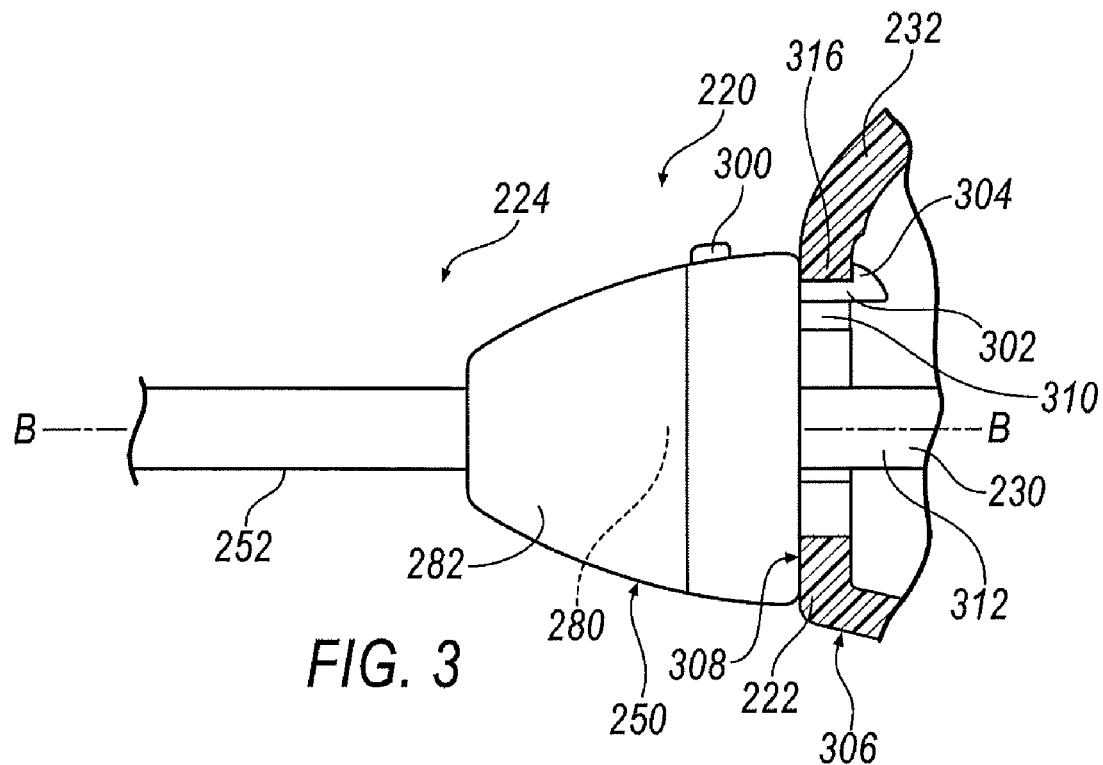
FIG. 3 is a side view of a portion of a medical system according to another embodiment.

Referring now to the drawings, the preferred illustrative embodiments of the present invention are shown in detail.

Although the drawings represent some preferred embodiments of the present invention, the drawings are not necessarily to scale and certain features may be exaggerated to better illustrate and explain the present invention. Further, the embodiments set forth herein are not intended to be exhaustive or otherwise limit or restrict the invention to the precise forms and configurations shown in the drawings and disclosed in the following detailed description.

FIG. 1 illustrates a medical system 20. The medical system 20 includes a medical device, or biopsy device 22 (illustrated partially) and an introducer 24 generally defining an axis A-A. The biopsy device 22 includes a cutting element 30 sized for introduction into a patient's body and extends from a hand piece 32. The cutting element 30 includes an outer cannula 36 defined by a first outer lumen 38 and a first inner lumen 40, and an inner cannula 44 sized to fit concentrically within the first inner lumen 40. A motor or other motion generating device (not shown) may be provided with the hand piece 32 to rotate and/or translate inner cannula 44 within outer cannula 36. Biopsy apparatus similar to device 22 can be seen by way of example in U.S. Pat. Nos. 6,638,235 and 6,744,824, which are owned by the assignee of the present invention and are incorporated herein by reference in their entirety.

In the embodiment illustrated, the outer cannula 36 of the biopsy device 22 includes a tissue piercing tip 46, such as a trocar tip, to facilitate penetration of the system 20 into a patient's tissue. In addition to a trocar tip, it will be appreciated that the outer cannula 36 may include other devices for piercing the patient's tissue, including without limitation, devices that use a laser or radio frequencies (RF) to pierce the tissue.

As best seen in FIG. 2, the introducer 24 includes an introducer hub 50, an introducer cannula 52, and a latch portion 56. As will be described in detail, system 20 is particularly, but not necessarily, suited for use in biopsy procedures that identify the target biopsy site using Magnetic Resonance Imaging (MRI) or comparable medical imaging modality. The introducer 24 may be made of a MRI compatible, medical grade material, such as 316 stainless steel or Inconel™ 625.

The introducer cannula 52 includes a generally cylindrical body 58 having a distal end 60, a proximal end 62, an introducer outer lumen 64, and an introducer inner lumen 66. The distal end 60 defines a distal introducer opening 70. The hub 50 includes a generally annular hub portion 76, a hemostatic valve 80, and the latch portion 56. The annular hub portion 76 includes a hub outer surface 82, a hub inner surface 84, a hub distal end 86, and a hub proximal end 88. The hub inner surface 84 includes a generally cylindrical introducer cannula mating surface 90 and a generally cylindrical valve mating surface 92. The latch portion 56 includes a release button 100 and a latch 102 extending generally parallel to the axis A-A having a latch tab 104 extending generally perpendicular to and toward the axis A-A.

As best seen in FIG. 1, the biopsy device 22 includes a device distal end 106 defined by a distal surface 108, and a latch portion, or latch opening, 110. The latch opening 110 includes a latch tab interference portion 112.

As best seen in a comparison of FIGS. 1 and 2, the hemostatic valve 80 includes a body 120 that is a self-sealing membrane that will permit a medical device, such as the biopsy device 24 or a site marker deployment device, to pass therethrough while sealing around the medical device and will reseal with itself after the medical device is removed from the valve 80.

A medical device, such as the biopsy device 22 partially interposed within the introducer 24, may include a vacuum source (not shown). The vacuum source may aspirate the biopsy site where the biopsy device 22 removes a tissue sample.

The length of the outer cannula 36, from the distal surface 108 to the piercing tip 46 is identified by the reference character "M" in FIG. 1. The length of the introducer 24 from the distal end 60 to the hub proximal end 88 is identified by the reference character "I" in FIG. 1.

Figure 4:
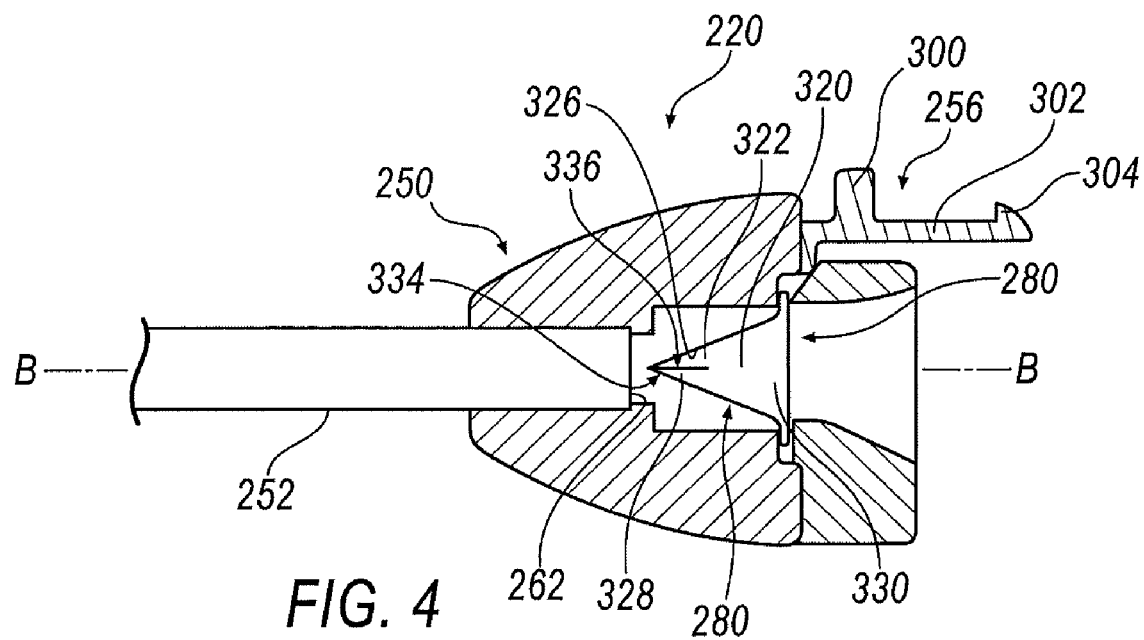
FIG. 4 is a partially sectioned side view of the medical system of FIG. 3.
Figure 7:
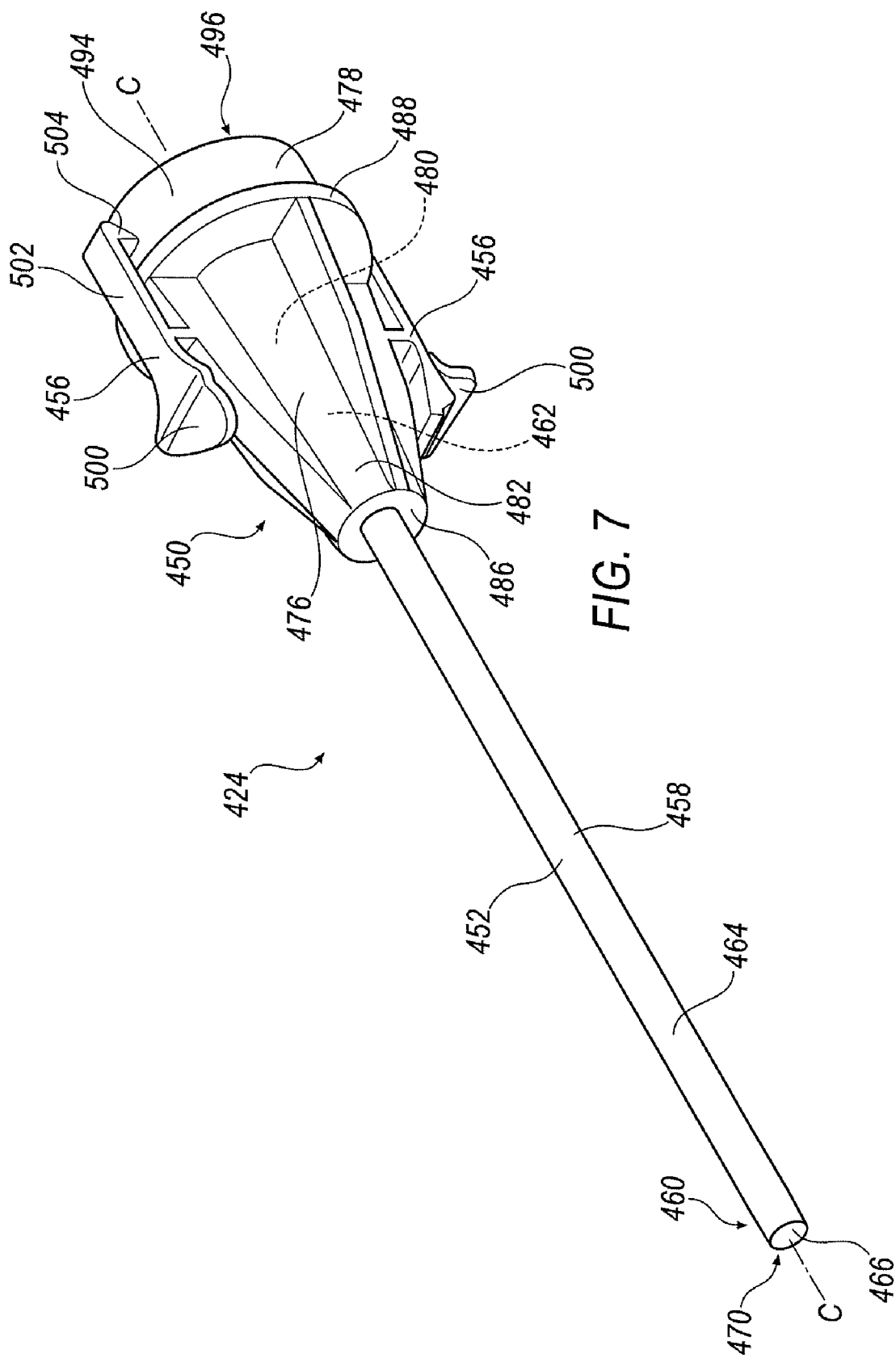
FIG. 7 is a perspective view of a portion of the medical system of FIG. 6.

FIGS. 3-5 illustrate an alternative embodiment of the medical system 20 as a medical system 220. The medical system 220 includes a medical device, or biopsy device 222 (illustrated partially in FIGS. 3 and 5) and an introducer 224 generally defining an axis B-B. The biopsy device 222 includes a cutting element 230 that extends from a hand piece 232. The cutting element 230 includes an outer cannula 236 defined by a first outer lumen 238 and a first inner lumen 240, and an inner cannula 244 sized to fit concentrically within the first inner lumen 240. A motor or other motion generating device may be provided with the hand piece 232 to rotate and/or translate inner cannula 244 within outer cannula 236.

In the embodiment illustrated, the outer cannula 236 of the biopsy device 222 includes a tissue piercing tip 246, such as a trocar tip, to facilitate penetration of the system 220 into a patient's tissue. In addition to a trocar tip, it will be appreciated that the outer cannula 236 may include other devices for piercing the patient's tissue, including without limitation, devices that use a laser or radio frequencies (RF) to pierce the tissue.

As best seen in FIG. 4, the introducer 224 includes a hub 250, an introducer cannula 252, and a latch portion 256. As will be described in detail, system 220 is particularly, but not necessarily, suited for use in biopsy procedures that identify the target biopsy site using Magnetic Resonance Imaging (MRI) or comparable medical imaging modality.

As best seen in FIG. 5, the introducer cannula 252 includes a generally cylindrical body 258 having a distal end 260, a proximal end 262, an introducer outer lumen 264, and an introducer inner lumen 266. The distal end 260 defines a distal introducer opening 270. The hub 250 includes a generally annular hub portion 276, a hemostatic valve 280, and the latch portion 256. The annular hub portion 276 includes a hub outer surface 282, a hub inner surface 284, a hub distal end 286, and a hub proximal end 288. The hub inner surface 284 includes a generally cylindrical introducer cannula mating surface 290 and a generally cylindrical valve mating surface 292. The latch portion 256 includes a release button 300 and a latch 302 extending generally parallel to the axis B-B having a latch tab 304 extending generally perpendicular to the axis B-B.

As best seen in FIG. 3, the biopsy device 222 includes a device distal end 306 defined by a distal surface 308, a latch opening 310, and an outer cannula sheath 312. The latch opening 310 includes a latch tab interference portion 316.

As best seen in a comparison of FIGS. 4 and 5, the hemostatic valve 280 includes a body 320 having a slit 322 formed therein. The slit 322 generally segregates the body 320 into a first flap 326 and a second flap 328 interconnected at an outer periphery, or outer edge, 330 such that the slit 322 does not intersect the outer edge 330. The first flap 326 is defined by a first flap opening surface 334, and the second flap 328 is defined by a second flap opening surface 336. The first flap opening surface 334 and the second flap opening surface 336 are formed so as to flex inwardly until the first flap opening surface 334 and the second flap opening surface 336 bindingly contact (FIG. 4) and provide a seal for the introducer inner lumen 266. To provide this resilient flexing for a self-sealing effect, the valve 280 may be made of a silicone or other suitable material that will bias the first flap 326 and the second flap 328 toward a closed position.

The first flap opening surface 334 and the second flap opening surface 336 are in contact in the closed position of FIG. 4 and provide a seal for the introducer inner lumen 266 when the valve 280 does not have a medical device interposed therein. In FIG. 5, the first flap opening surface 334 and the second flap opening surface 336 contact the first outer lumen 238 so as to form a seal therebetween and restrict fluids from leaking therepast and through the introducer cannula 252. In the embodiment illustrated, the hemostatic valve 280 is not punctured with each use, but is a valve having a defined opening.

FIGS. 6-9 illustrate an alternative embodiment of the medical system 20 as a medical system 420. The medical system 420 includes a medical device, or site marker deployment device 422 (illustrated partially in FIG. 9) and an introducer 424 generally defining an axis C-C.

As best seen in the embodiment of FIG. 9, the site marker deployment device 422 includes a deployment handpiece 430, a deployment rod 432, and a deployment cannula 434 extending therefrom. The deployment cannula 434 includes a generally cylindrical body 436 having a distal deployment end 438 defined, at least in part, by a distal deployment opening 440, a proximal deployment end 442, a deployment inner lumen, or inner surface, 444, and a deployment outer lumen, or outer surface, 446. In the embodiment illustrated, the deployment inner lumen 444 and the deployment outer lumen 446 are generally cylindrical.

The deployment cannula 434 is illustrated in FIG. 9 with a site marker 448 (illustrated in phantom) interposed therein. The site marker 448 may be an MRI identifiable marker, such as a collagen plug, metal spring, or other medical treatment. The deployment rod 432 extends at least partially through the hand piece 430 and the deployment cannula 434 and is used to urge the site marker 448 through the distal deployment opening 440 when the deployment device 422 is desirably positioned, as discussed in greater detail below.

As best seen in FIGS. 6-9, the introducer 424 includes a hub 450, an introducer cannula 452, and a pair of latch portions 456. As will be described in detail, system 420 is particularly, but not necessarily, suited for use in biopsy procedures that identify the target biopsy site using Magnetic Resonance Imaging (MRI) or comparable medical imaging modality.

As best seen in FIG. 8, the introducer cannula 452 includes a generally cylindrical body 458 having a distal end 460, a proximal end 462, an introducer outer lumen 464, and an introducer inner lumen 466. The distal end 460 defines a distal introducer opening 470. The hub 450 includes a generally annular hub portion 476, a first portion, or collar, 478, a hemostatic valve 480, and the latch portions 456. The annular hub portion 476 includes a hub outer surface 482, a hub inner surface 484, a hub distal end 486, and a hub proximal end 488. The hub inner surface 484 includes a generally cylindrical introducer cannula mating surface 490 (FIG. 9) and a generally cylindrical valve mating surface 492 (FIG. 9). The collar 478 includes a generally cylindrical outer surface 494 and a generally annular collar end surface 496. The hub proximal end 488 includes a generally cylindrical hub flange 498. Each latch portion 456 includes a release button 500 and a latch 502 extending generally parallel to the axis C-C having a latch tab 504 extending generally perpendicular to the axis C-C.

As best seen in FIG. 9, the deployment handpiece 430 of the site marker deployment device 422 includes a deployment distal end 506 defined by a deployment distal surface 508. The deployment distal end 506 has a pair of latch openings 510 and a collar opening 512 formed therein. Each latch opening 510 includes a latch tab interference portion 514. The collar 478 is received within the collar opening 512. The hemostatic valve 480 may be a valve 80 or a valve 280, as desired.

FIG. 6 illustrates the introducer 424 with a medical device, or a biopsy device 528 interposed therein. The biopsy device 528 includes a cutting element 530 sized for introduction into the patient's body. The cutting element 530 extends from a handpiece 532. The cutting element 530 includes an outer cannula 536 defined by a first outer lumen 538 and a first inner lumen 540, and an inner cannula 544 sized to fit concentrically within the first inner lumen 540. A motor or other motion generating device may be provided with the hand piece 532 to rotate and/or translate inner cannula 544 within outer cannula 536.

In the embodiment illustrated, the outer cannula 536 of the biopsy device 528 includes a tissue piercing tip 546, such as a trocar tip, to facilitate penetration of the system 520 into a patient's tissue. In addition to a trocar tip, it will be appreciated that the outer cannula 536 may include other devices for piercing the patient's tissue, including without limitation, devices that use a laser or radio frequencies (RF) to pierce the tissue.

The handpiece 532 includes a biopsy device distal end 550 having a biopsy device distal surface 552 for abutting the collar 478 to restrict the movement of the introducer 424 relative to the biopsy device 528. When the biopsy device 528 and the introducer 424 are coupled such as shown in FIG. 6, the length of the biopsy device 528, from the collar end surface 496 to the piercing tip 546 is identified by the reference character "A2" in FIG. 6.

The length of the introducer 424 from the distal end 460 to the collar end surface 496 is identified by the reference character "B2" in FIGS. 6 and 9. When the deployment device 422 and the introducer 424 are coupled such as shown in FIG. 9, the length of the deployment device 422, from the collar end surface 496 to the distal deployment opening 440 is identified by the reference character "C2" in FIG. 9. The length of the introducer 424 from the distal end 460 to the hub proximal end 488 is identified by the reference character "D" in FIG. 9. When the deployment device 422 and the introducer 424 are coupled such as shown in FIG. 9, the length of the deployment device 422, from the hub proximal end 488 to the distal deployment opening 440 is identified by the reference character "E" in FIG. 9.

In operation, a biopsy device, such as the biopsy device 528 is coupled with the introducer 424 such that the outer cannula 536 is interposed within the introducer cannula 452 with the piercing tip 546 extending from the distal introducer opening 470, as generally shown in FIG. 6. The biopsy device 528 is inserted into the introducer 424 until the collar end surface 496 contacts the biopsy device distal surface 552. In this biopsy configuration, the system 420 may be inserted into a patient's tissue to remove a tissue sample from a biopsy site. Also in this biopsy configuration, the valve 480 seals the introducer cannula such that fluids are restricted from flowing from the distal end 460 to the proximal end 462.

Next, the system 420 is inserted into a patient's tissue to a desired depth. This desired depth may be determined by viewing the system with a MRI during insertion. With the cutting element 530 positioned as desired, a tissue sample is drawn into the outer cannula 536 and separated from the surrounding tissue to form a biopsy site. A vacuum drawn through the outer cannula 536 may be applied to facilitate a complete separation and collection of the tissue sample.

Next, the biopsy device 528 is removed from the tissue as the introducer 424 is maintained in a relatively stable position relative to and within the tissue. As the piercing tip 546 passes the valve 480, the valve 480 seals with itself to restrict a loss of fluids from the biopsy site. In the embodiment described, the valve 480 is a valve 280 where the first flap opening surface 334 and the second flap opening surface 336 flex inwardly until the first flap opening surface 334 and the second flap opening surface 336 bindingly contact (FIG. 4) and provide a seal for the introducer inner lumen 466.

Next, the deployment device 422, with a site marker 448 interposed therein, may be inserted into the introducer 424 (FIG. 9). The deployment device 422 is inserted into the introducer 424 until the deployment distal surface 508 contacts the hub proximal end 488. The deployment cannula 434 is sized to fit within the introducer cannula 452, but need not be snugly fit, since the valve 280 will reduce leakage therebetween.

The site marker 448 may then be deployed by urging the site marker out of the introducer 424 through the distal introducer opening 470. Deployment devices for deploying a site marker may be found in U.S. Pat. No. 7,044,957.

The deployment device 422 and the introducer 424 may be removed simultaneously by urging the deployment handpiece 430 away from the tissue generally in a direction parallel to the axis C-C since the deployment device 422 is latched to the introducer 424. Alternately, the deployment device 422 may be unlatched from the introducer 424 by urging the release buttons 500 inwardly toward the axis C-C to disengage the latch tabs 504 from the latch openings 510 and urge the deployment device 422 away from the introducer 424.

As illustrated and described herein the valve 280 (which may be commonly referred to as a duck bill valve) will permit medical devices to be inserted therethrough while restricting the flow of fluids therethrough. Either a biopsy device or a site marker deployment device, or both, could be latched to an introducer using a latch as described herein, as desired. The latches described herein permit a medical device to be positioned relative to an introducer hub in a desirable, confirmable position for performing a treatment, such as removing tissue or deploying a site marker or other treatment. An introducer hub, such as the introducer hub 50, 250, 450 may be positioned relative to the tissue by an indicator on the introducer outer lumen 464, or a support grid affixed to a MRI device. Additionally, the operation of the systems 20, 220 are similar to the system 420, with variations in whether the biopsy device or the deployment device (or both) are latched and unlatched from the introducer hub, as desired.

FIGS. 10-14 illustrate embodiments of the system 20 with adjusting mechanisms for accommodating cannula of differing lengths. That is, briefly, biopsy devices and marker deployment devices may be supplied with lengths of, for example, 10 centimeters (cm), 12 cm, or 14 cm. While introducers with lengths of 10, 12, and 14 cm may be supplied, a user may require a 12 cm introducer cannula for a biopsy device (such as the dimension B2 of the biopsy device 22 of FIG. 6) and a 14 cm introducer cannula for a site marker deployment device (such as the dimension B2 of the site marker deployment device of FIG. 9).

Since the introducer is generally not removed during the procedure of removing a biopsy device and deploying a marker for precision of marker positioning, the user may attempt to insert the deployment device partially, estimate when the deployment device is 2 cm from full insertion into an introducer (where full insertion is shown FIG. 9), and deploy the marker. This method may not provide the desired precision of marker positioning. Further, a user may stock multiple deployment devices having cannula of differing lengths to precisely deploy a marker depending upon the cannula length of the biopsy device employed.

Figure 10:
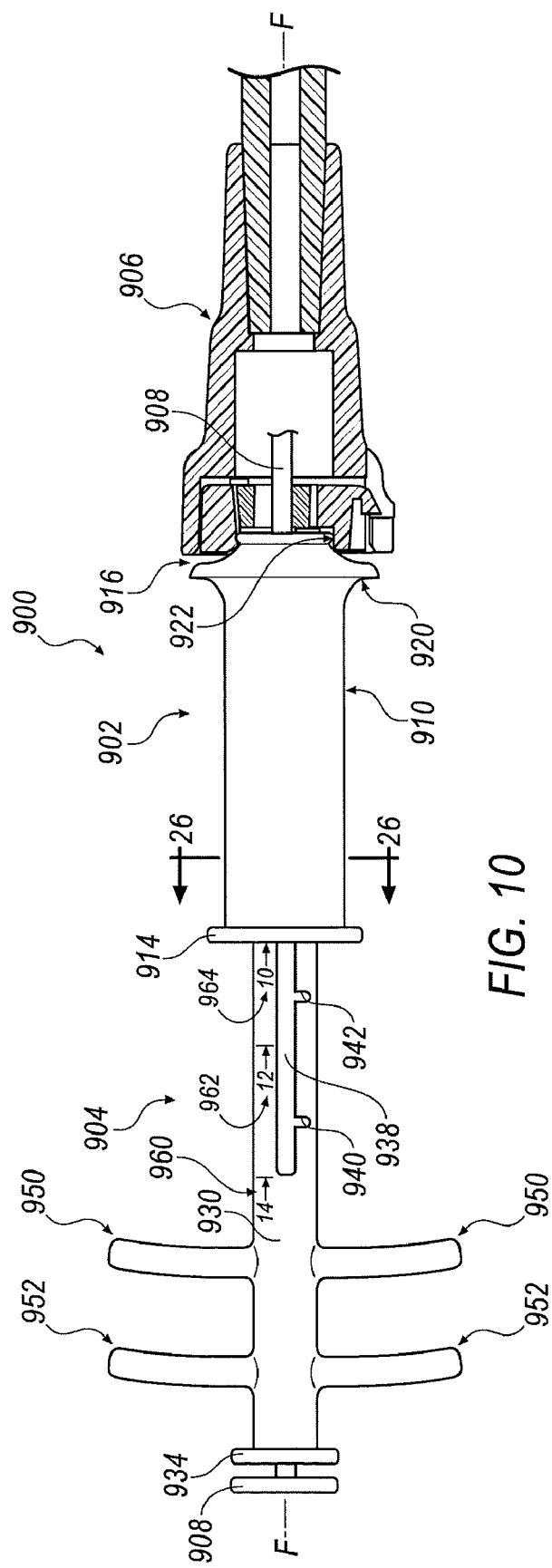
FIG. 10 is a partially sectioned side view of a medical system according to a further embodiment.
Figure 11:
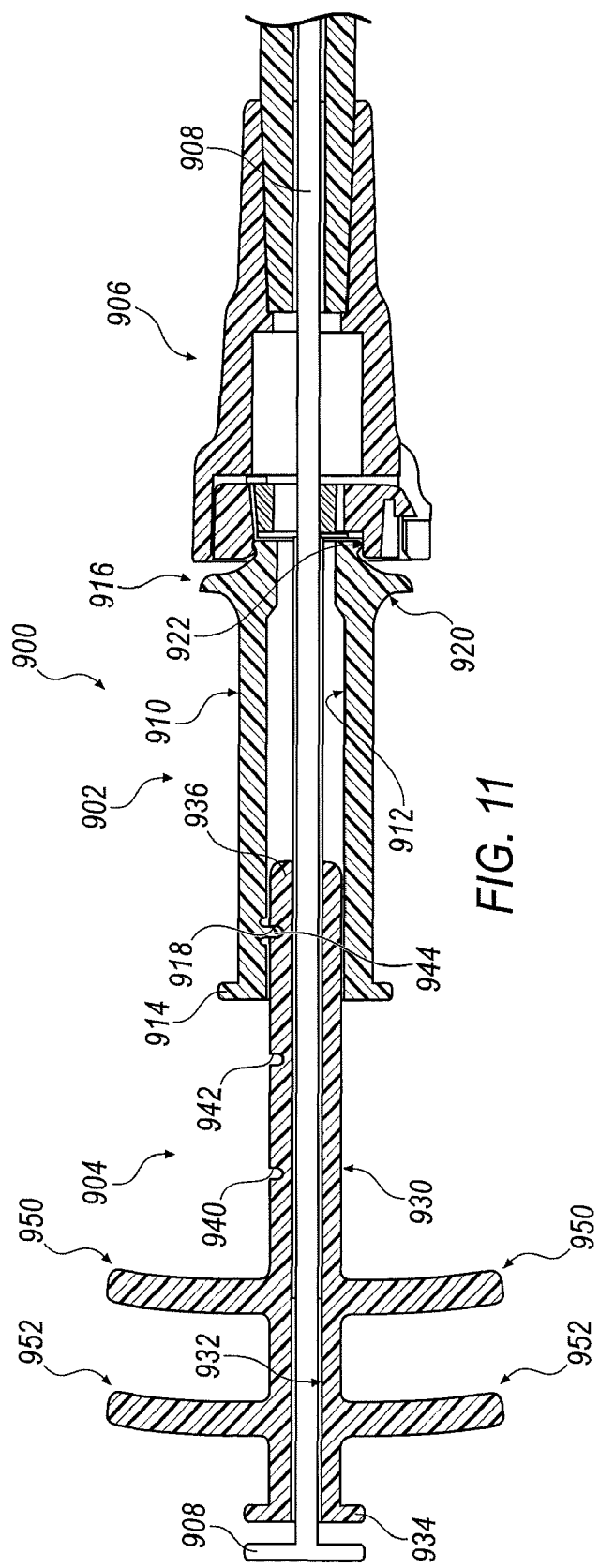
FIG. 11 is a sectioned side view of the medical system of FIG. 10.
Figure 12:
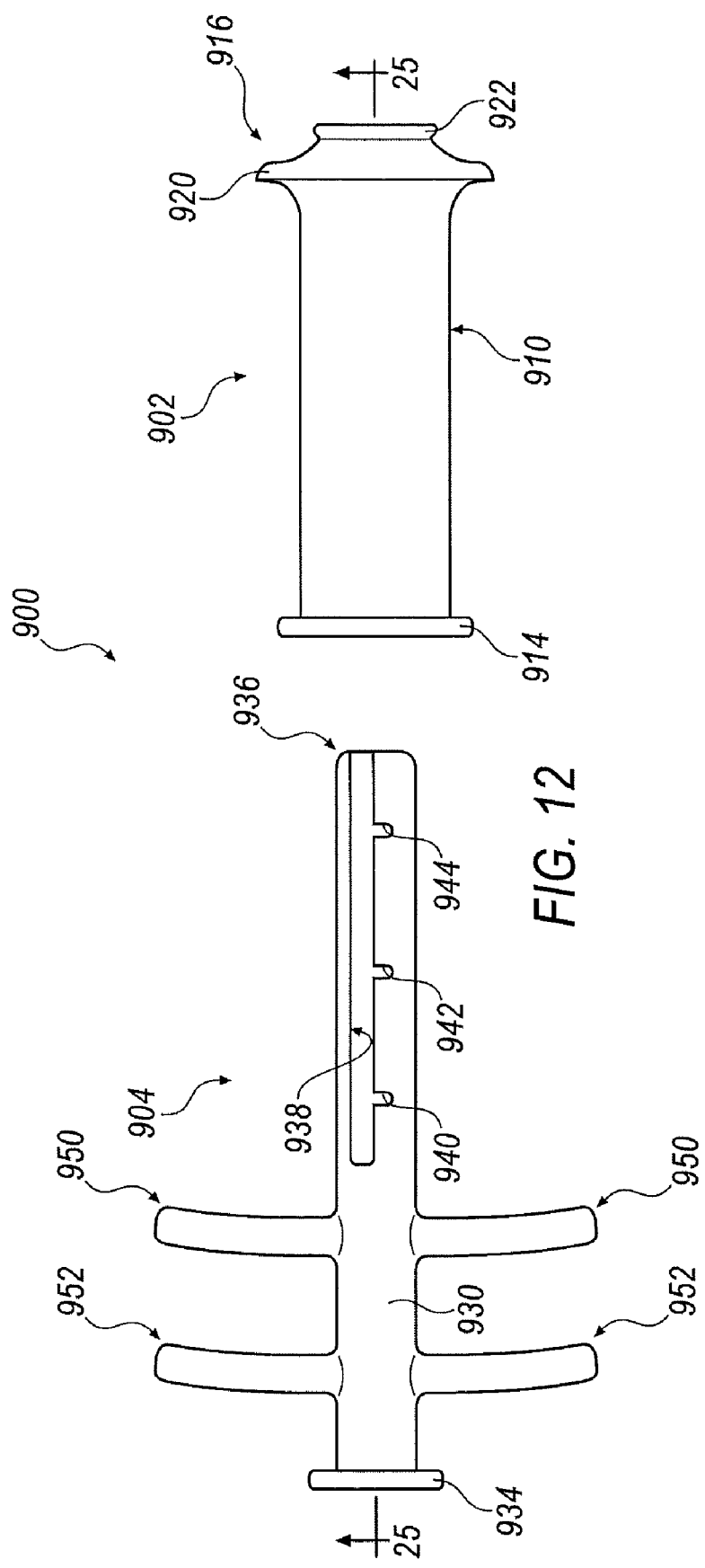
FIG. 12 is an exploded side view of the medical system of FIG. 10.
Figure 13:
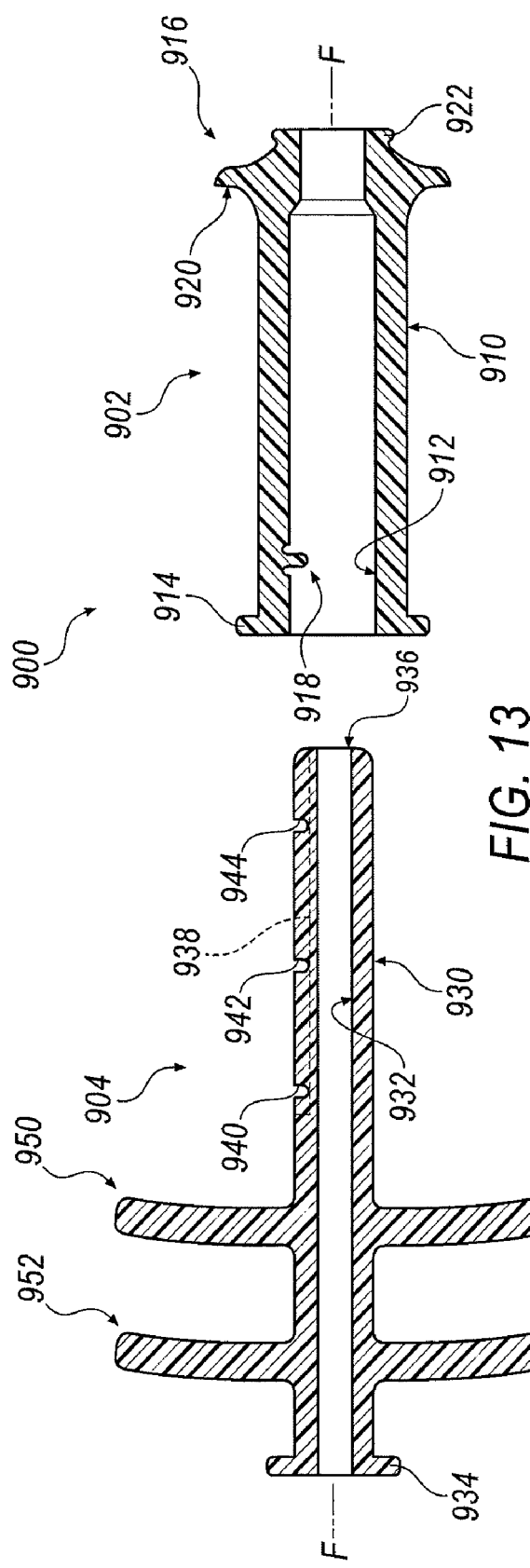
FIG. 13 is a sectioned exploded side view of the medical system of FIG. 10.

FIGS. 10-14 illustrate another embodiment of a spacer for a medical device as a spacer 900. The spacer 900 includes an outer hub 902 and an inner hub 904. FIGS. 10 and 11 illustrate the spacer 900 coupled to an introducer 906 and having a push rod 908 interposed therein, while FIGS. 12 and 13 illustrate exploded views of the spacer 900.

The outer hub 902 includes a generally cylindrical outer surface 910, a generally cylindrical inner surface 912, an outer hub proximal end 914, an outer hub distal end 916, and a locating finger 918 (FIGS. 11, 13, and 14) extending radially inward. The outer hub distal end 916 includes a generally cylindrical first latch surface 920 and a second latch surface 922. In the embodiment illustrated, the outer hub distal end 916 is similar to the hub distal end 844 of the spacer 830, in that a plurality of introducer hubs, such as the introducer hubs 50, 250, 450, 650, 770, 824 may be releasably coupled thereto.

The inner hub 904 includes generally cylindrical outer surface 930, a generally cylindrical inner surface 932, an inner hub proximal end 934, an inner hub distal end 936, an axial guide slot 938 (FIGS. 10, 12, 13 and 14), a first circumferential locking slot 940, a second circumferential locking slot 942, and a third circumferential locking slot 944. In the embodiment illustrated, the inner hub 904 also includes a plurality of first handles 950 and a plurality of second handles 952 extending generally radially therefrom.

Figure 14:
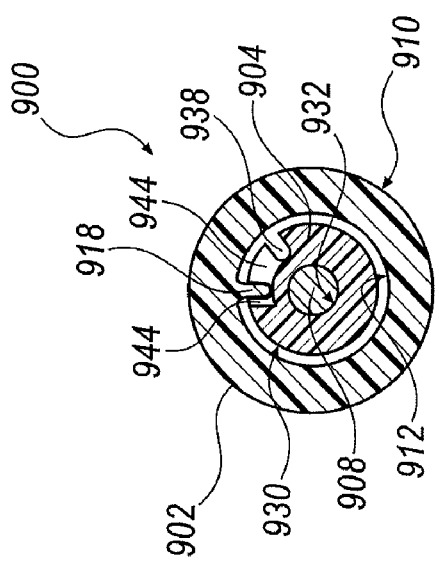
FIG. 14 is a view of the medical system of FIG. 10 taken along line 26-26 of FIG. 10, enlarged for clarity.

As best seen in FIG. 13, the axial guide slot 938, the first circumferential locking slot 940, the second circumferential locking slot 942, and the third circumferential locking slot 944 do not intersect the inner surface 932. As best seen in FIGS. 11 and 14, the axial guide slot 938, the first circumferential locking slot 940, the second circumferential locking slot 942, and the third circumferential locking slot 944 receive the locating finger 918. That is, the locating finger 918 is guided by the axial guide slot 938 as the inner hub 904 moves axially relative to the outer hub 902, and the locating finger 918 may be interposed within one of the first circumferential locking slot 940, the second circumferential locking slot 942, and the third circumferential locking slot 944. The locating finger 918 is interposed within one of the slots 940, 942, 944 as the inner hub 904 is rotated relative to the outer hub 902. When the locating finger 918 is interposed within one of the first circumferential locking slot 940, the second circumferential locking slot 942, and the third circumferential locking slot 944, the inner hub 904 is restrained from moving axially relative to the outer hub 902. In this manner, the spacer 900 can provide a variable length between the outer hub distal end 916 and inner hub proximal end 934, as desired.

The spacer 900 may be provided with indications 960, 962, 964 (FIG. 10), to indicate which slot 940, 942, 944, the finger 918 is adjacent to, or locked into. For example, the indication 960 may indicate a desired position for the end 914 of the outer hub 902 to be positioned when a 14 cm introducer is coupled to the spacer 900, and the indication 964 may indicate a desired position for the end 914 of the outer hub 902 to be positioned when a 10 cm introducer is coupled to the spacer 900.

While the spacer 900 is illustrated with a push rod 908 interposed therein, any medical device, such as a biopsy device 22, 222, deployment device 422, or a biopsy device 528 may be inserted therein. The finger 918 provides a first interference surface, the first circumferential locking slot 940 provides a second interference surface, the second circumferential locking slot 942 provides a third interference surface, and the third circumferential locking slot 944 provides a fourth interference surface. In use, the first interference surface of the finger 918 interferes with one of the second interference surface, the third interference surface, or the second circumferential locking slot 942 provides a fourth interference surface to restrain relative axial movement between the inner hub 904 and the outer hub 902.

In addition to the deployment rod 432 (FIG. 9), the push rod 908 (FIGS. 10 and 11) may be used as a target confirmation device, such as a stylet or localizing obturator, for a cannula end, such as the distal end 60 of cannula 52, the distal end 460 of cannula 452. That is, the end of a target confirmation device, when positioned adjacent the distal end of a cannula, will be visible under modalities such as a MRI, and will help a user to confirm where the end of the cannula is positioned relative to a lesion when the device is inserted through the cannula. In other words, the use of target confirmation device with an imaging modality confirms that treatment, such as a marker, will be placed where it is intended.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A medical system, comprising:
a first medical device having a first medical device engaging end;
an introducer including an introducer cannula having a proximal end and a distal end; and
an axial distance adjustment system for providing an adjustable distance between at least a portion of the first medical device end and the introducer cannula distal end,
wherein the adjustment system includes an inner member and an outer member, wherein one of the inner member and the outer member includes a first interference surface, the other of the inner member and the outer member includes a second interference surface and a third interference surface, the inner member is at least partially interposed within the outer member and selectively axially moveable therebetween, and wherein the inner member and the outer member are selectively restrained from axial movement therebetween when the first interference surface contacts one of the second interference surface and the third interference surface.

2. The system of claim 1, further comprising:
a second medical device having a second medical device engaging portion,
wherein at least one of the inner member and the outer member of the adjustment system is coupled to the introducer and the other of the inner member and the outer member is coupled to one of the first medical device and the second medical device.

3. The system of claim 1, wherein at least one of the inner member and the outer member includes an axially extending surface portion and at least a portion of the first interference surface will selectively guide along the axially extending surface portion.

4. The system of claim 1, wherein the introducer includes a latch portion, and a hub, wherein the cannula is defined, at least in part, by an inner lumen, the latch portion is adapted to releasably secure the introducer to a medical device, the hub includes a proximal end and a distal end.

5. The system of claim 1, wherein the adjustment system includes a plurality of indications to indicate a relative axial position of the inner member and the outer member.

6. The system of claim 5, wherein at least a portion of the plurality of indications corresponds to a length of the introducer.

7. The system of claim 1, wherein a latch portion extends from the proximal end of the introducer.

8. The system of claim 1, wherein the medical device includes a biopsy needle.

9. The system of claim 1, further comprising a hemostatic valve.

10. The system of claim 1, wherein the system is constructed of a material that is magnetic resonance imaging (MRI) compatible.

11. A medical system comprising:
a first medical device having an elongated cannula and an introducer engaging end;
an introducer having an introducer cannula and a hub having a hub proximal end and a hub distal end, wherein the introducer is defined, at least in part, by an introducer distal end and an introducer proximal end, and wherein the introducer proximal end is engaged with the medical device; and
an adjustment system for selectively providing an adjustable desired distance between at least a portion of the introducer proximal end and the introducer distal end for restricting axial movement therebetween,
wherein the adjustment system includes an inner member and an outer member, wherein one of the inner member and the outer member includes a first interference surface, the other of the inner member and the outer member includes a second interference surface and a third interference surface, the inner member is at least partially interposed within the outer member and selectively axially moveable therebetween, and wherein the inner member and the outer member are selectively restrained from axial movement therebetween when the first interference surface contacts one of the second interference surface and the third interference surface.

12. The system of claim 11, wherein at least one of the inner member and the outer member includes an axially extending surface portion and at least a portion of the first interference surface will selectively guide along the axially extending surface portion.

13. The system of claim 11, further comprising a latch extending from one of the introducer and the first medical device, wherein the latch will selectively engage the first medical device with the introducer so as to axially restrain at least a portion of the medical device relative to the introducer cannula during at least a portion of a medical procedure.

14. The system of claim 12, wherein the latch will engage the first medical device with the introducer as the first medical device cannula is interposed within the introducer cannula, and wherein the latch may be manipulated so as to disengage the first medical device from the introducer so as to permit the first medical device cannula to be withdrawn from the introducer cannula.

15. The system of claim 11, wherein the elongated cannula will selectively permit a medical treatment to be delivered through the introducer cannula.

16. The system of claim 11, wherein the elongated cannula will selectively capture a biopsy sample for removal through the introducer cannula.

* * * * *